US007965019B2

United States Patent
Gabl

(10) Patent No.: US 7,965,019 B2
(45) Date of Patent: Jun. 21, 2011

(54) DEVICE COMPRISING A PIEZOACOUSTIC RESONATOR ELEMENT AND INTEGRATED HEATING ELEMENT, METHOD FOR PRODUCING THE SAME AND METHOD FOR OUTPUTTING A SIGNAL DEPENDING ON A RESONANT FREQUENCY

(75) Inventor: Reinhard Gabl, St. Peter im Sulmtal (AT)

(73) Assignee: Siemens Aktiengesellschaft, Munich (DE)

( * ) Notice: Subject to any disclaimer, the term of this patent is extended or adjusted under 35 U.S.C. 154(b) by 450 days.

(21) Appl. No.: 12/063,108

(22) PCT Filed: Sep. 6, 2006

(86) PCT No.: PCT/EP2006/066087
§ 371 (c)(1),
(2), (4) Date: Apr. 1, 2008

(87) PCT Pub. No.: WO2007/028810
PCT Pub. Date: Mar. 15, 2007

(65) Prior Publication Data
US 2010/0134209 A1 Jun. 3, 2010

(30) Foreign Application Priority Data

Sep. 9, 2005 (DE) .......................... 10 2005 043 039

(51) Int. Cl.
*H01L 41/083* (2006.01)
(52) U.S. Cl. ...................................... 310/346; 310/320

(58) Field of Classification Search .................. 310/320, 310/346, 338
See application file for complete search history.

(56) References Cited

U.S. PATENT DOCUMENTS

| 5,212,988 A | 5/1993 | White et al. | |
|---|---|---|---|
| 5,587,620 A * | 12/1996 | Ruby et al. | 310/346 |
| 5,674,742 A | 10/1997 | Northrup et al. | |
| 5,696,423 A * | 12/1997 | Dydyk et al. | 310/346 |
| 7,196,405 B1 * | 3/2007 | Ferreiro et al. | 257/678 |
| 2005/0028336 A1 | 2/2005 | Robert et al. | |
| 2006/0125489 A1 | 6/2006 | Feucht et al. | |

FOREIGN PATENT DOCUMENTS

| DE | 196 44 290 A1 | 5/1998 |
|---|---|---|
| WO | 2004/017063 A2 | 2/2004 |
| WO | 2005/052554 A1 | 6/2005 |

OTHER PUBLICATIONS

Machine translation of WO2004/017063 generated by the website of the European Patent Office.*

(Continued)

*Primary Examiner* — Derek J Rosenau
(74) *Attorney, Agent, or Firm* — Young & Thompson

(57) ABSTRACT

A device includes at least one piezoacoustic resonator element (21-29) having at least one piezoelectric layer (21a-29a) and two electrodes (21b-29b, 21c-29c) applied to the piezoelectric layer (21a-29a). The piezoacoustic resonator element (21-29) is configured in such a manner that, when a voltage is applied to the piezoelectric layer (21a-29a) by electrodes (21b-29b, 21c-29c), a bulk wave of the piezoelectric layer (21a-29a) is induced with a resonant frequency. The device also includes a heating device with a heating element (211-219), integrated into the piezoacoustic resonator element (21-29), for controlling the working temperature of the device.

24 Claims, 6 Drawing Sheets

OTHER PUBLICATIONS

Ferrari et al., "Cavitand-coated PZT resonant piezo-layer sensors: properties, structure, and comparison with QCM sensors at different temperatures under exposure to organic vapors," Sensors and Actuators B, vol. 103, No. 1-2, p. 240-246 (Sep. 29, 2004).

Ruby et al., "Micromachined Thin Film Bulk Acoustic Resonators," 48th Freq Cont Symposium, pp. 135-138 (Jun. 1-3, 1994).

Dubois, "Thin film bulk acoustic wave resonators: a technology overview," Memswave 03 (Jul. 2-4, 2003).

* cited by examiner

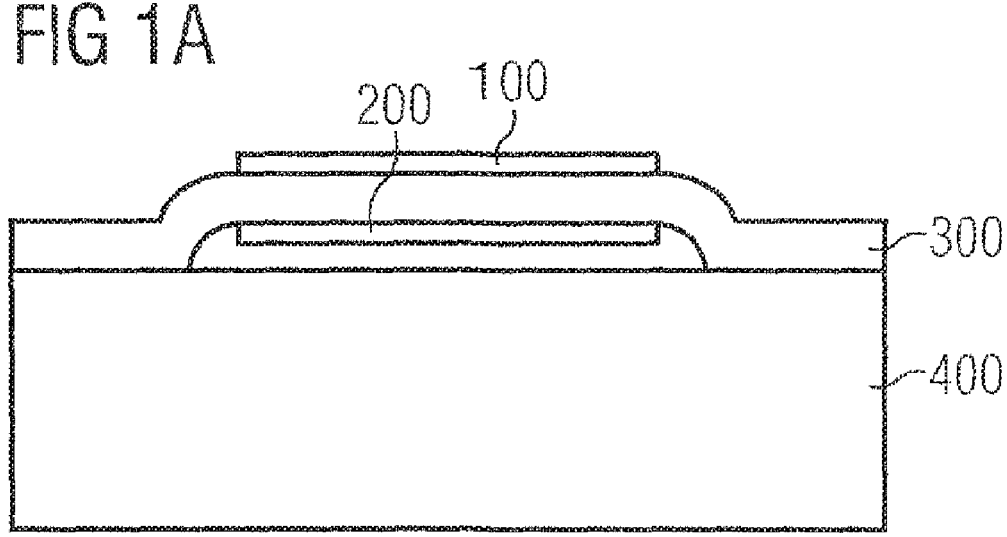
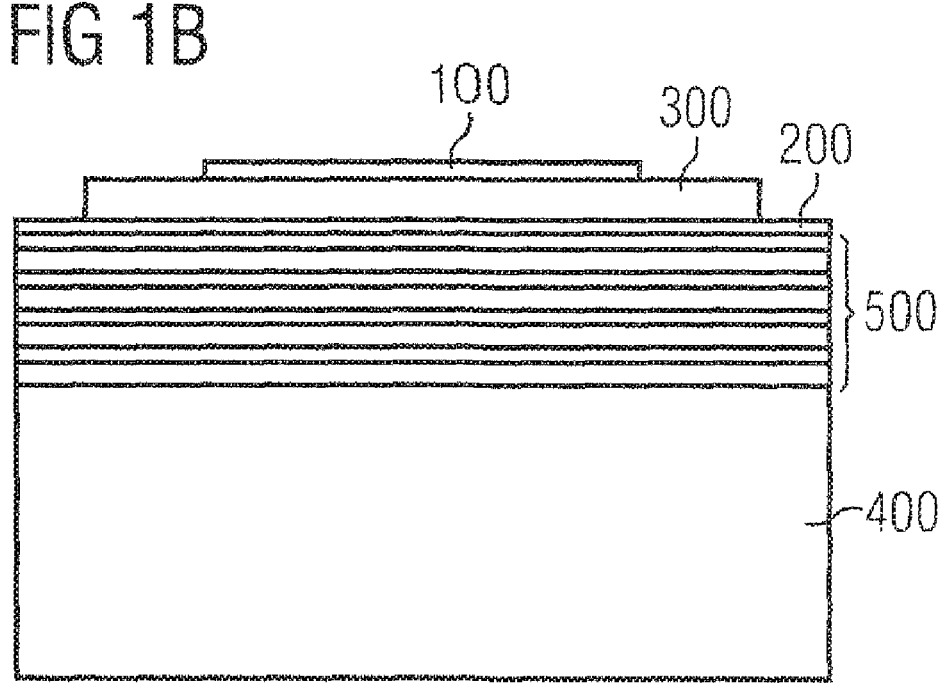

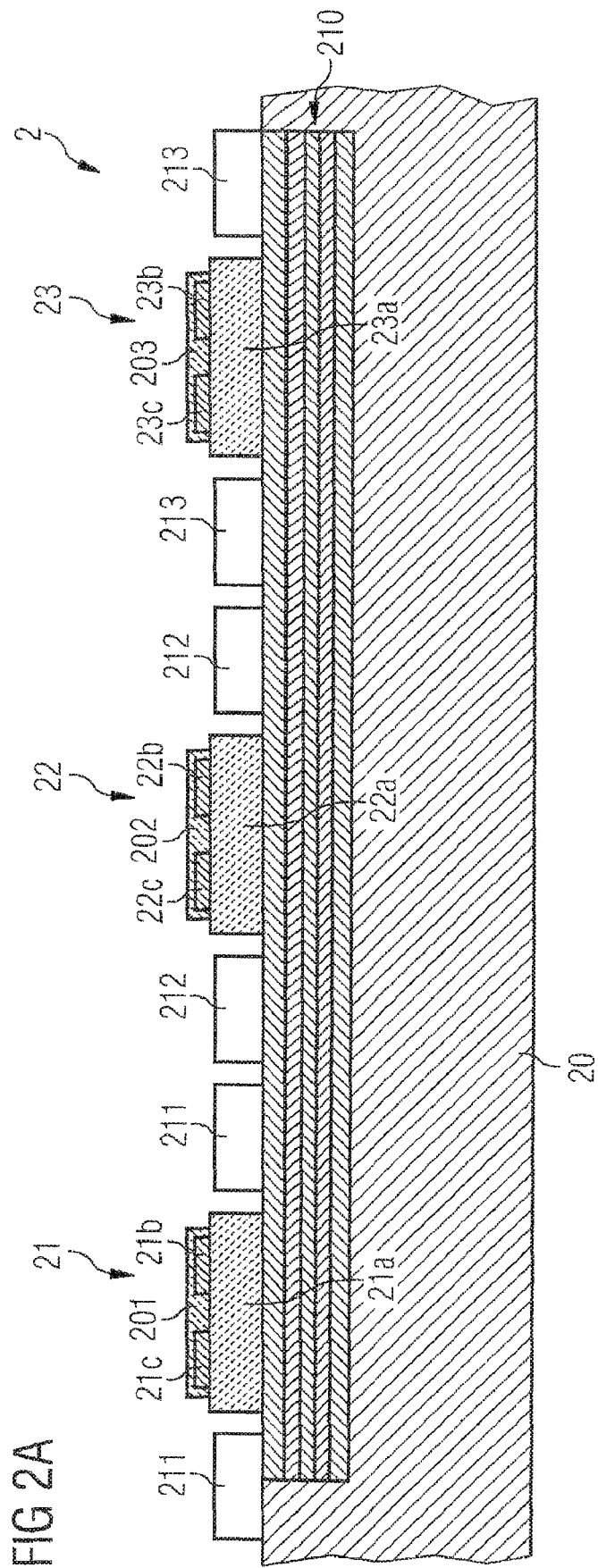

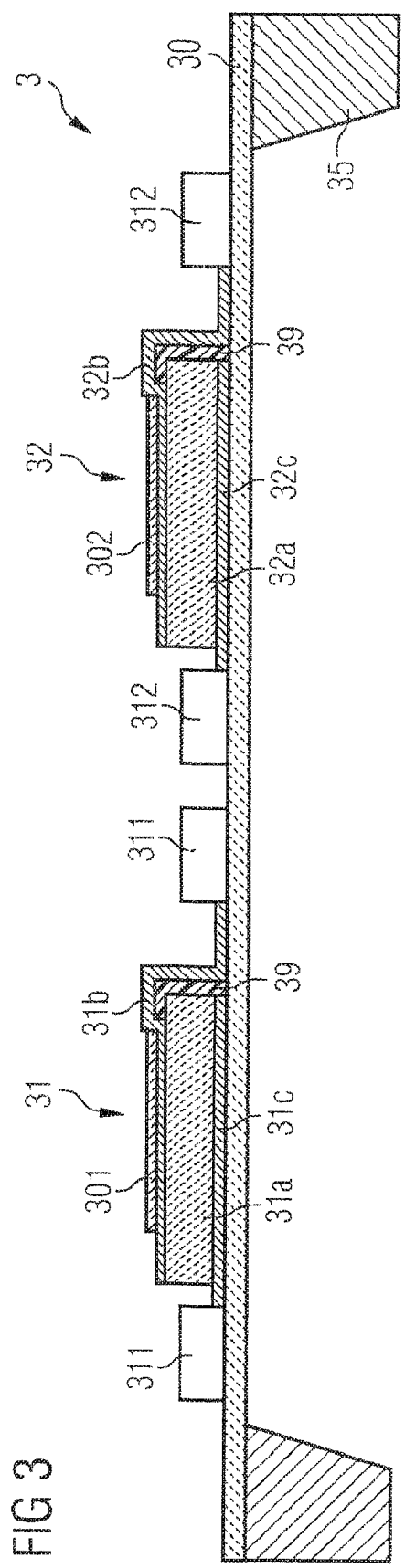

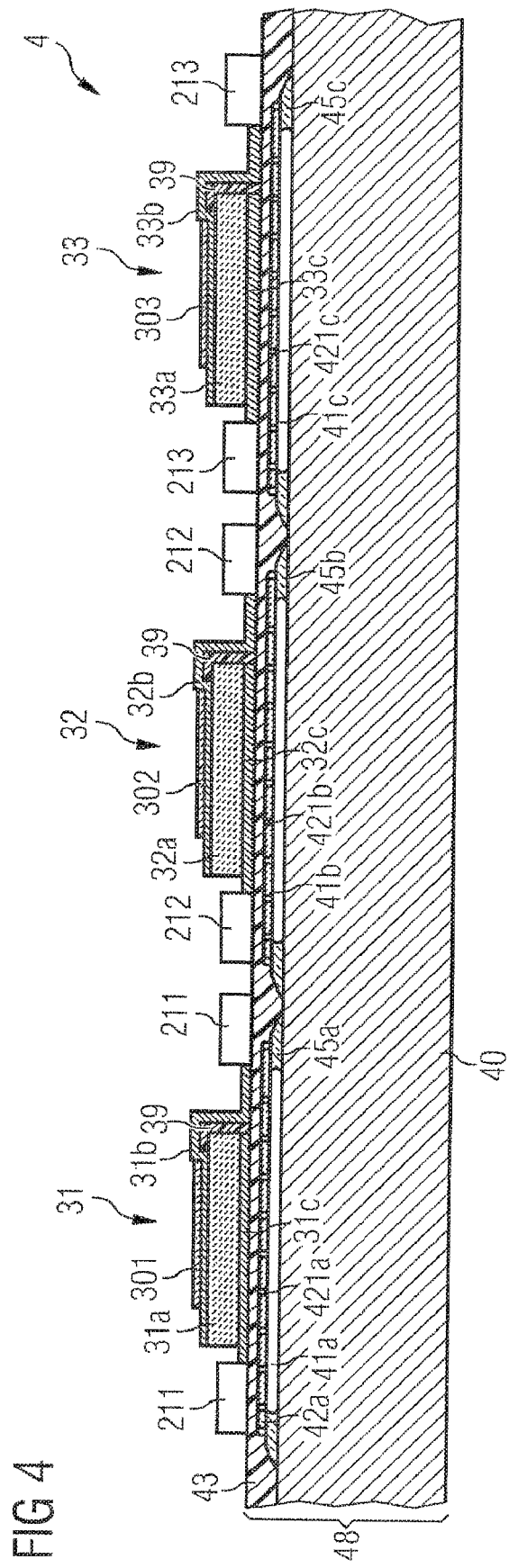

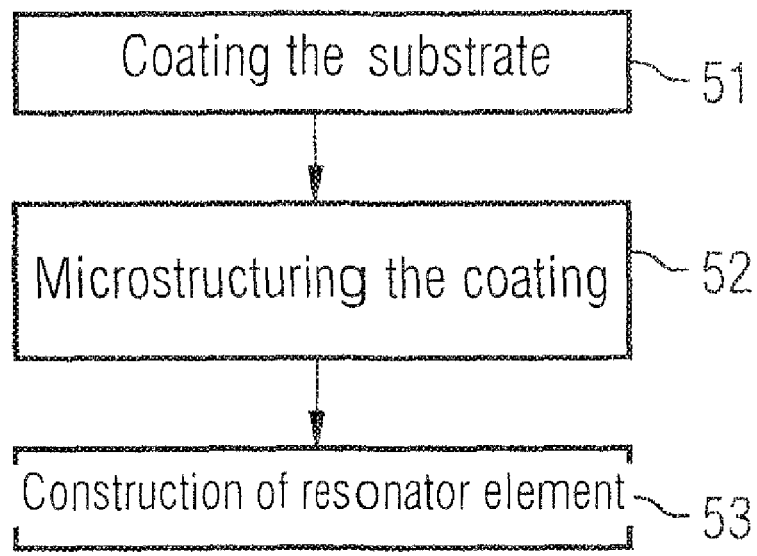
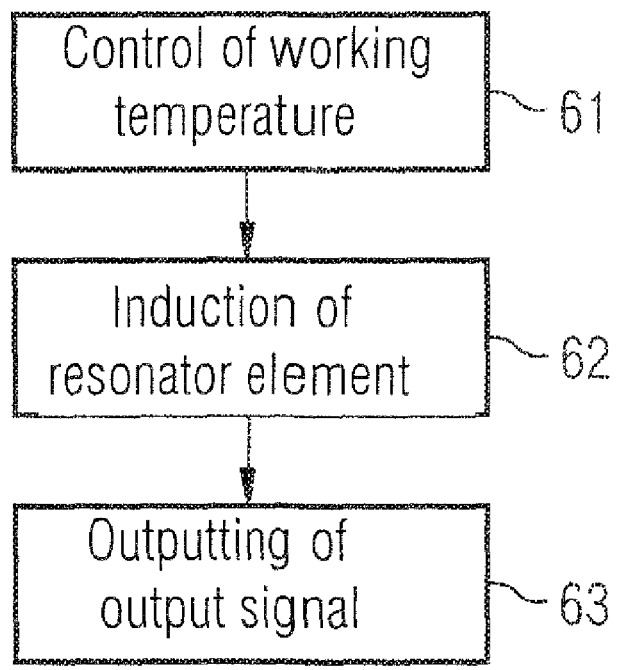

DEVICE COMPRISING A PIEZOACOUSTIC RESONATOR ELEMENT AND INTEGRATED HEATING ELEMENT, METHOD FOR PRODUCING THE SAME AND METHOD FOR OUTPUTTING A SIGNAL DEPENDING ON A RESONANT FREQUENCY

The invention relates to a device comprising at least one piezoacoustic resonator element with a piezoelectric layer and two electrodes applied to the piezoelectric layer, the piezoacoustic resonator element being configured in such a manner that when an alternating voltage is applied to the piezoelectric layer by means of the electrodes, a bulk wave of the piezoelectric layer is induced with a resonant frequency, to a method for producing a device of this kind and to a method for outputting a signal as a function of a resonant frequency.

Piezoacoustic resonator elements of this type in which a thickness mode of vibration, i.e. a bulk acoustic wave, of the piezoelectric layer is induced with resonant frequency when an alternating voltage field is applied, have become known by the English name "Bulk Acoustic Wave (BAW) Piezoelectric Resonator" and were primarily developed for high-frequency applications in communications electronics.

The simplest configuration for producing a BAW resonator is a layer made of a piezoelectric material which with appropriate crystallographic orientation, for example with the c axis perpendicular to a surface of the electrode, is arranged between two electrodes in a sandwich structure.

FIGS. 1 and 2 schematically show two basic types of BAW resonators, as disclosed in the overview by M. Dubois "Thin Film Bulk Acoustic Resonators: A Technology Overview", published on the occasion of the MEMSWAVE 03 conference, Toulouse, France, Jul. 2-4, 2003.

FIG. 1A schematically shows an example of what is known as a "Thin Film Bulk Acoustic Resonator" (FBAR). A piezoelectric AlN layer 300 is applied to a carrier substrate in the form of an Si wafer 400. Electrodes 100 and 200 are attached to the lower and upper sides of the piezoelectric layer. If an electric alternating field is applied to the piezoelectric layer 300 by the electrodes 100/200, the electrical energy is converted into mechanical energy due to the inverse piezoelectric effect. The resulting acoustic bulk wave propagates inside the piezoelectric layer, the direction of progress being parallel to the electrical field and the wave being reflected at the electrode/air interface. The sympathetic oscillation is achieved if the thickness of the layer structure of the resonator is equal to half the wave length of the input signal. To avoid acoustic losses in the carrier substrate a cavity is provided on the lower side of the piezoelectric layer, so the acoustic waves can be reflected at the electrode/air interface.

FIG. 1B shows a construction of a BAW resonator as what is known as a Solidly Mounted Resonator (SMR). In contrast to the construction of FIG. 1 an acoustic reflector (Bragg reflector) 500 is provided between the lower electrode 300 and the substrate 400 to avoid acoustic losses in the direction of the carrier substrate. This acoustic reflector comprises a plurality of layers with very different acoustic impedance and which are arranged in alternating sequence, for example layers of W/SiO$_2$ or Al/AlN, etc. The layer thickness is $\lambda/4$.

Compared with what are known as surface acoustic wave resonators (SAW resonators) that have already been used as filter elements for a relatively long time in high-frequency engineering, a basic difference lies in the fact that in the case of BAW resonators a thickness mode of vibration (bulk wave) of the piezoelectric layer is induced in contrast to surface acoustic waves in the case of surface acoustic wave resonators. A bulk wave (bulk acoustic wave) is induced by suitable arrangement of electrodes combined with suitable crystallographic orientation of the piezoelectric layer. Depending on the configuration the induced bulk wave of the piezoacoustic resonator element can be a longitudinal vibration or a thickness shear mode of vibration.

This basic difference between surface acoustic wave resonators (SAW resonators) and bulk acoustic wave resonators (BAW resonators) has significant effects on the electrical properties of the components, depending on the field of application. By way of example: when using BAW resonators as filter elements in the high frequency range there is only minimal coupling to electric fields outside of the metal surfaces owing to the electrical field generated between the two electrodes. FBAR and BAW filters also exhibit lower electrical losses in the passband than OFW filters and are also considerably more power compatible than these.

Particular advantages also result in relation to production technology since BAW resonators may be easily integrated as a carrier substrate on a semiconductor chip using standard IC technologies (for example CMOS, BiC-MOS, etc.).

Basically thick film technology, which is substantially based on screen printing methods and is particularly suitable for structures in the range of >100 µm, and thin film technology, such as deposition from the vapor phase via CVD/PVD methods, may be considered as the production technology for BAW resonators, however.

Owing to the fact that structures in the size range clearly below 10 µm through to the sub-µm range are accessible by way of thin film technology, this is particularly expedient with respect to the requirements of increasing integration and advancing miniaturization of the various components.

Reactive sputtering is described by way of example as the production technology for BAW resonators in the publication by Marc-Alexandre Dubois, Thin Film Bulk Acoustic Wave Resonators: A Technology Overview, MEMS Wave 03, Toulouse, France, Jul. 2-4, 2003, cited in the introduction, as the production process for the growth of aluminum nitride layers as the piezoelectric layer on corresponding electrodes. As described in this publication a 1.8 µm thick AlN layer with a piezoelectric coefficient of $d_{33,f}$ of 5.3±0.22 pm/V may be produced by reactive sputtering, and this points to the high quality of the AlN layer produced by the sputtering process.

Apart from AlN basically ZNO, PZT (lead zirconate titanate) or lithium niobate for example may be used as the piezoelectric layer, AlN having advantages in relation to its chemical, electrical and mechanical properties however, but in particular also as far as integration on a semiconductor chip (already discussed) is concerned.

As mentioned in the introduction, BAW resonators were originally developed as passive components for high-frequency engineering, in particular for systems in the target range of 1 to 10 GHz. The production of voltage-controlled oscillators (VCO) or amplifiers (Low Noise Amplifier, LNA) in particular should be mentioned as application examples.

In addition to the use as components in high-frequency engineering, use of a BAW resonator as a sensor has been proposed. By way of example application WO 2004/017063 A2 belonging to the Applicants describes a sensor for detecting the absorption of a specific substance on the surface of the BAW resonator. The relevant substance may thus be identified. Absorption can denote adsorption or absorption in this case.

Structurally the resonator comprises a sensitive coating for this purpose, for example in the form of a polymer film, which is applied to an electrode of the resonator. Various substances, for example hydrocarbons, can be absorbed on this polymer film. The substance to be detected is located in a fluid (gas or liquid) which is used as the medium for measuring. For measurement the sensor is brought into contact with the medium for measuring and which contains the substance which can be absorbed on the sensitive coating. A microfluid with measuring cell is conventionally used, by way of which the medium for measuring flows past the relevant surface portion of the sensor.

The surface portion of the sensor, at which the relevant substance is absorbed, is in many cases guided by the type of substance to be detected in order to be able to thus selectively detect a specific substance from a mixture of a plurality of substances. By way of example the above-cited patent application describes detection of DNA fragments by means of a sensor which on a surface portion of the electrode has a coating with a selected DNA sequence that allows absorption of suitable DNA sequences according to the key-lock principle.

In the detection of DNA it is critical that strands with a mono- or polybasic mismatch can be distinguished from a perfect match (complementary strand). This crucially depends on the state of equilibrium of desorption of the DNA strands at the surface portion. This state of equilibrium of desorption is determined by the conditions of the corresponding system, such as the type of coating, concentration of the participating species, temperature, etc.

Absorption of a substance on the resonator changes the resonant frequency as a function of the mass of the absorbed substance. By measuring the resonant frequency conclusions may thus be made about the absorption of a substance. The relevant characteristic value is the mass sensitivity of the resonator which is proportional to the square of the resonant frequency of the resonator.

In said patent application the positive effect of an extremely low layer thickness of the piezoelectric layer in the range of 0.1 µm to 20 µm is described, and this has a positive effect on the detection sensitivity of the sensor owing to the pronounced connection between mass sensitivity and resonant frequency. Advantages also result in relation to integration density and miniaturization, in particular in the case of sensor arrays which contain a plurality of sensor elements of this kind.

The object of the invention is to disclose an improved device comprising at least one piezoacoustic resonator element of the type mentioned in the introduction and a simple and inexpensive method for producing a device of this kind. A particular object of the present invention is to provide a device of this kind which is configured as a sensor for detection of a substance with increased measuring accuracy and an expanded field of application.

An object of the invention is furthermore to disclose an optimized method for outputting a signal as a function of a resonant frequency of a piezoacoustic resonator.

This object is achieved by a device with piezoacoustic resonator element with the features of claim 1 and a production method with the features of claim 22. An optimized method for outputting a signal as a function of a resonant frequency of a piezoacoustic resonator is disclosed in claim 23.

Preferred embodiments of the invention are described by the dependent claims.

According to the invention the device comprises a heating device with a heating element that is integrated into the piezoacoustic resonator element for controlling the working temperature of the device.

The working temperature of the device according to the present invention can be the temperature of the piezoacoustic resonator element. The invention is not limited to this however. The site of the working temperature of the device can be any desired portion of the device itself and/or a surrounding portion close to the device.

In particular when the device is configured as a sensor for detection of a substance the working temperature can relate to the surface portion at which the substance to be detected is absorbed. The temperature of the medium for measuring, in which the substance is located, can also constitute a working temperature of the device according to the present invention.

To integrate the heating device with the piezoacoustic resonator element the heating element of the heating device is advantageously constructed as a layer. This layer can substantially be made from a material which can be constructed as a resistance heater for heating the device.

The thickness of the layer is advantageously in the range below 25 µm. A layer thickness is particularly preferably <10 µm and most preferably a layer thickness is <1 µm. A low layer thickness promotes integration of the heating element by use of thin film technology methods, such as deposition methods via PVD/CVD processes. This makes it particularly easily possible to process the heating element together with the piezoacoustic resonator element.

In a simple configuration of the device according to the invention the heating element constructed as a layer is formed together with piezoacoustic resonator element on a carrier substrate.

Interlayers can be arranged between the layer-like heating element and the carrier substrate. For example the piezoacoustic resonator element and the heating element can be arranged on interlayers using the layer technique and function as an acoustic reflector (Bragg reflector) which is intended to reduce acoustic loss in the direction of the substrate.

In a particularly simple and advantageous embodiment the carrier substrate is constructed as a membrane which can be produced for example by back etching a semiconductor substrate with an $SiO_2$ or $Si_3N$ layer as the etching stop. Alternatively the membrane can cover a cavity in the carrier substrate, i.e. be constructed as a surface micromechanism, as shown in FIG. 1A.

In BAW resonators the use of a membrane provides acoustic insulation to prevent the induced oscillation propagating into the carrier substrate and leading to acoustic losses. By arranging the heating element on a membrane thermal insulation of the device is provided on the back, and this minimizes the required heating power since backward heat diffusion and thermal losses caused thereby can be almost completely prevented.

When the heating element is arranged together with the piezoacoustic resonator element on a membrane this results in the particular advantage of it being possible to simultaneously achieve acoustic and thermal insulation.

In addition to the heating element the heating device can contain conventional functional elements for operating the heating element, such as connecting means with external power supply, etc.

In a particularly advantageous embodiment of the present invention the heating element comprises a plurality of mutually joined sections which are arranged in such a way that the resonator element and/or its surroundings can be heated from a plurality of sides of the resonator element. In a particularly preferred exemplary embodiment these sections are laterally arranged with equal spacing from edge portions of the resonator, so along its edge the resonator element is encompassed by the sections of the heating element. The spacing between the heating element and the piezoelectric layer of the piezoacoustic resonator is preferably less than 100 µm, more preferably less than 50 µm and most preferably less than 10 µm.

According to the invention an electrode of the piezoacoustic resonator element itself may also be used as the heating element.

The heating element can be produced by conventional thick film technology techniques. An improved facility for integration and miniaturization results however when using thin film technologies known from semiconductor technology to produce layer thicknesses in the sub-µm range through to the nm range. These may be conventional PVD/CVD methods in this connection.

As far as the nature of the material of the heating element is concerned, a material is preferably used which can be operated as a resistance heater. The use of metals which can also act as a metal resistance thermometer is particularly advantageous. In this case the heating element can also be operated as a temperature measuring element in which the device is configured to determine the temperature from the resistance value of the heating element, which acts as a temperature measuring element in this case. Platinum should be mentioned in particular in this connection, of which the temperature coefficient of the resistance is from $3.85 \cdot 10^{-3}/^\circ$ C. in an operative range from $-200$ to $+850^\circ$ C. Nickel may also be used if the temperature to be measured does not exceed $150^\circ$ C. Nickel offers advantages over platinum in particular with respect to the lower price.

A device of this kind in which a heating device and a temperature sensor are constructed so as to be integrated with the piezoacoustic resonator element can comprise an evaluation device with a storage device in which the corresponding characteristic curve of the temperature dependency of the resistance for the given material is stored, and a read-out device for reading out a temperature value as a function of the acquired resistance value. Evaluation device and read-out device can be components of an external device which is suitably electrically connected to the piezoacoustic resonator element and the temperature detection device. According to the present invention a conventional wireless connection can be electrically connected, and this is not limited to conventional wiring.

Configuration of the device with a temperature detection device (microsensor) and heating device allows closed temperature regulation of the working temperature of the piezoacoustic resonator element which includes control of the temperature by the heating device, detection of the working temperature and subsequent regulation of the working temperature as a function of the detected temperature.

Effective temperature compensation of the resonant frequency for example can thus be effected by ensuring that the device is operated at a pre-defined temperature.

Particular advantages result for the case where the device according to the invention is configured as a sensor for detection of a substance, since by controlling the temperature the equilibrium conditions of absorption of the substance to be detected at the surface portion of the piezoacoustic resonator element can be purposefully controlled. The accuracy of the measured value detection can thus be increased, depending on the substance to be detected. At the same time the operative range of the sensor can be increased since the absorption conditions, which in addition to the temperature are determined by the medium for measuring (gas, liquid), by the substance to be detected and further substances that are possibly present in the medium for measuring, can be purposefully influenced. Detection of substances, which for example are only absorbed on the surface portion of the sensor at a pre-defined temperature, is thus achievable.

"Detection of a substance" according to the present invention can be used to identify a substance. The sensor can however also be constructed as a mass sensor for example to determine an absorbed quantity.

In this connection it can be advantageous for the heating device to be located in a position on the sensor element which ensures that the heating device is in contact with the medium for measuring. Effective heating of the medium for measuring, which flows for example through a flow cell of the sensor, can be achieved hereby.

The invention also includes a production process for producing a device according to the invention. In this method a carrier substrate is coated with a metal layer. An electrode of the piezoacoustic resonator element and the heating element are subsequently created by microstructuring this metal layer. The fundamental aspect in this connection is that part of the piezoacoustic resonator element and the heating element can be produced by microstructuring just one metal layer in one operation. Photolithographic methods, as are basically known from semiconductor technology, are particularly suitable for microstructuring.

The method according to the invention allows significant streamlining of the manufacturing process since the added expenditure is extremely low and is substantially limited to adaptation of the layout.

In a particularly advantageous embodiment platinum is applied to the substrate, for example by deposition from the vapor phase. Owing to its temperature dependency of resistance platinum is also suitable as a resistance thermometer, so an electrode of the resonator element, a heating element of the heating device and a measuring element of a temperature detection device can be produced in one method step by microstructuring the applied layer.

This is particularly advantageous especially where the device is configured as a sensor for detecting the absorption of a substance since the desired temperature for absorption of a predetermined substance can thus be precisely regulated, i.e. controlled and measured, in the vicinity of the device, in particular in the region of the surface portion for absorption of the substance.

All three functional elements: heating element, measuring element and electrode, can be produced by the same layer portion, which is activated in different ways, in this case.

The resonator and the heating elements can be contacted, for example as a module, with a high-frequency substrate (for example LTCC—(Low Temperature Cofired Ceramics) substrate) via the carrier substrate by bondpads using flip chip technology. This is used to improve the electrical properties of the high-frequency component since inductances of corresponding connecting wires can be avoided. Flip chip technology, which is basically known from semiconductor technology, also allows an increased packing density of the various components and therewith makes a significant contribution to improved integration and miniaturization when producing whole HF modules.

The invention also includes a method for outputting a signal, which depends on a resonant frequency, comprising the steps of controlling by way of a heating element the working temperature of a piezoacoustic resonator element of a device comprising at least one piezoacoustic resonator element with a piezoelectric layer and two electrodes in electrical contact with the piezoelectric layer, the piezoacoustic resonator element being configured in such a manner that by applying an alternating voltage to the piezoelectric layer via the electrodes an acoustic bulk wave of the piezoelectric layer is induced with resonant frequency; inducing a bulk wave of the piezoelectric layer of the piezoacoustic resonator element with resonant frequency and outputting an output signal as a function of the measured resonant frequency.

In a particularly advantageous exemplary embodiment of the method according to the invention the method is for detection of a substance and is preferably carried out using the device according to the invention. This method includes the steps of combining the fluid and the piezoacoustic resonator in such a way that the substance can be absorbed and/or adsorbed at a portion of the resonator, and determining a resonant frequency of the resonator, it being possible to conclude from the resonant frequency the quantity of substance that has been absorbed in the surface portion. In the method according to the invention the working temperature of the device is controlled using the piezoacoustic resonator element before the step of determining the resonant frequency.

In the method according to the invention the working temperature of the device can also advantageously be measured using a corresponding piezoacoustic resonator element. This takes place in a particularly simple manner by way of the above-described device in which a temperature measuring element and a heating element are simultaneously integrated with each other. The method can include the step of regulating the working temperature, i.e. control as a loop as a function of the measured temperature.

The accuracy of the sensor can thus be increased considerably, depending on the substance to be detected. The method also makes it possible to detect specific substances for example which cannot be detected at ambient temperature.

The present invention provides the following advantages in particular:

An additional required element can be integrated on the carrier substrate (chip) with the heating element with little additional expenditure and processing.

The inventive construction of the device primarily takes account of integration particularly in the case of highly miniaturized systems.

In contrast to a discrete solution the heating element can be brought very close to the piezoacoustic resonator, whereby the volume for heating can be reduced and the heating power lowered thereby. This can be of considerable advantage precisely in the case of sensors that can be read wirelessly.

A temperature sensor can simultaneously be provided by evaluating the resistance of the heating element, in particular when platinum is used. This allows complete temperature regulation.

The temperature sensitivity of the resonant frequency can be taken into account by adjusting a working temperature of the piezoacoustic resonator element.

Advantageous embodiments and further details of the present invention will be described hereinafter with the aid of various exemplary embodiments and with reference to the figures.

FIGS. 1A and 1B schematically show in cross-section the construction of a FBAR and SMR resonator as examples of BAN resonators that are known from the prior art.

FIG. 2A schematically shows in cross-section the construction of an exemplary embodiment of the device according to the invention with integrated heating device.

FIG. 3 shows the schematic construction of a second exemplary embodiment of the device according to the invention in cross-section.

FIG. 4 shows the schematic construction of a third exemplary embodiment of the device according to the invention in cross-section.

FIG. 5 shows a flow diagram of an exemplary embodiment of a method for producing the device according to the invention.

FIG. 6 shows a flow diagram of an exemplary embodiment of a method according to the invention for outputting a signal value that depends on a resonant frequency.

Figure 2B:
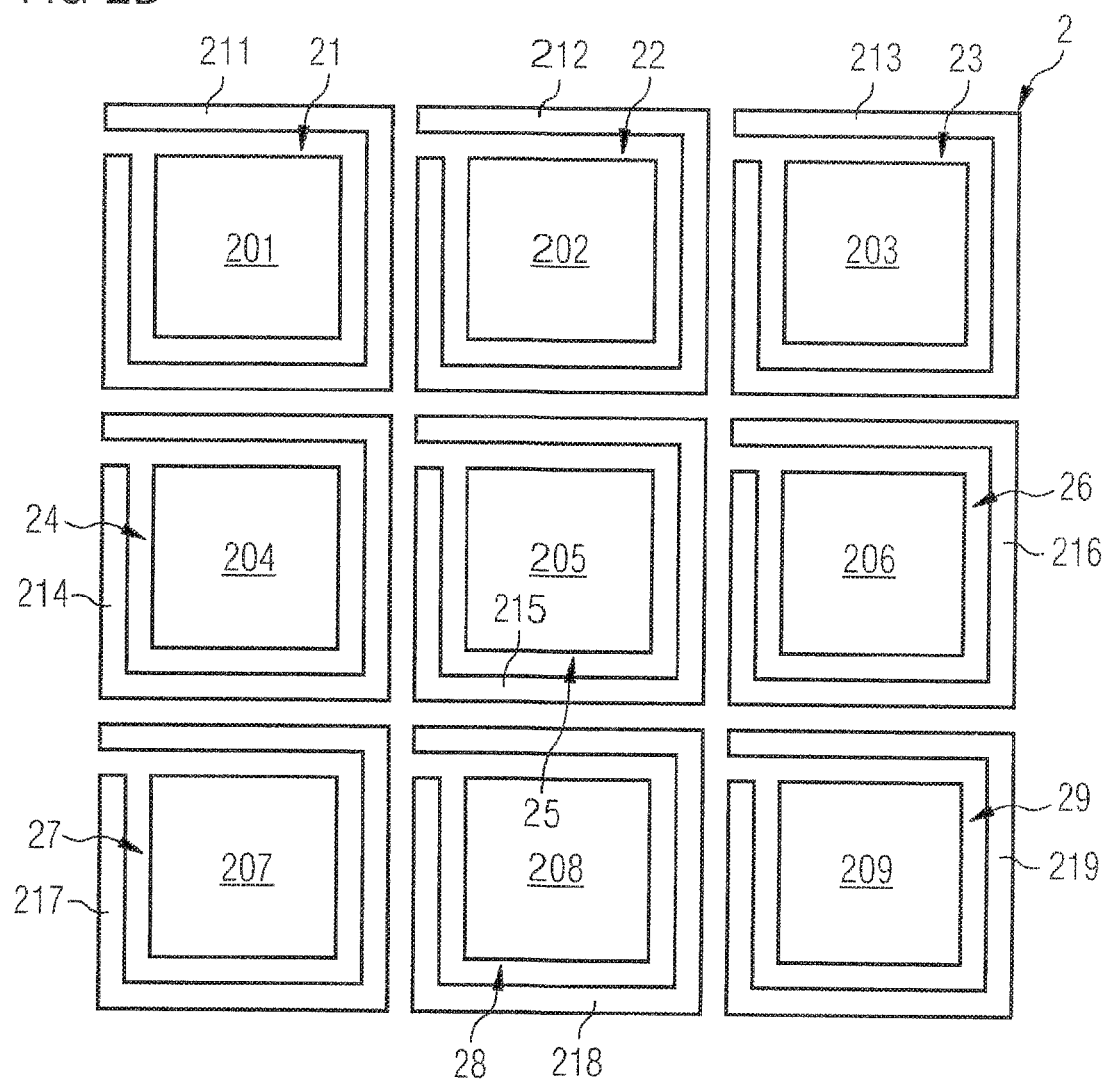
FIG. 2B shows a plan view of the first exemplary embodiment of the invention shown in FIG. 1.

The exemplary embodiment of the device according to the invention shown in FIGS. 2A and 2B relates to a 3×3 sensor array 2, comprising nine individual sensor elements 21-29. The individual elements 21-29 are each formed by a piezoacoustic resonator element with a piezoelectric layer $21a$, $22a$, $23a$ made of AlN and two electrodes $21b$, $22b$, $23b$ and $21c$, $22c$, $23c$ that are applied to the piezoelectric layer $21a$, $22a$, $23a$. The electrodes are made of Pt. In the first exemplary embodiment shown in FIG. 2 the two electrodes $21b$, $22b$, $23b$ and $21c$, $22c$, $23c$ are arranged on the upper side of the piezoelectric layers $21a$, $22a$, $23a$. The resulting bulk wave is a thickness shear mode of vibration.

In the plan view of FIG. 2b a sensor face with coating 201-209 can be seen from above respectively, at which face the substance of the medium for measuring that is to be detected can be absorbed. In the present exemplary embodiment this is a chemically sensitive coating comprising a specific DNA sequence. A corresponding DNA sequence can link up with this DNA sequence according to the key-lock principle, so selectivity with respect to a mixture of various DNA sequence is given. The corresponding DNA sequence can be chemically absorbed on the coatings 201-209 while forming hydrogen bridge compounds.

The individual sensor elements 21-29 are arranged on a semiconductor substrate 20. An acoustic reflector 210 which comprises $\lambda/4$ thick individual layers that have very different acoustic impedance is provided between the semiconductor substrate 20 and the individual sensor elements 21-29. The reflector 210 is used as a Bragg reflector for reducing the acoustic losses in the direction of the carrier substrate.

Although not explicitly shown in FIG. 2 an evaluation device for determining the resonant frequency can be integrated in the semiconductor substrate. The corresponding circuits (oscillating circuit for reading out the resonant frequency) that are known per se can be implemented by conventional semiconductor technologies, such as bipolar or CMOS technologies. The device can thus be constructed as a complete measuring module in the form of what is known as a "lab on a chip".

A plurality of heating elements 211-219 are arranged on the semiconductor substrate 20 and, as may be seen from FIG. 2B, comprise the individual sensor elements 21-29 in a square. The lateral spacing d between the inner edge of the heating elements 211-219 and the outer edge of the sensor elements 21-29 is 50 µm in the present exemplary embodiment but can also be less than this, for example be less than 10 µm. The layer thickness of the platinum strip conductors, which form the heating elements 211-219, is 500 nm in this exemplary embodiment, the width is 2 µm.

Symmetrical arrangement of the heating elements 211-219 in relation to the sensor elements 21-29 ensures that all sensor elements 21-29 can be used at the same working temperature.

Although in the schematic diagram of FIG. 2a the heating elements 211-219 have approximately the same thickness as the coated piezoacoustic resonator elements 21-29, reference is made to the fact that this diagram is not to scale and the thickness of the heating elements 211-219 is in the range of the layer thickness of the lower electrode $21c$ in many applications.

FIG. 3 shows a cross-section of a second embodiment of a device according to the invention which is configured as a 2×2 sensor array 3. The construction of this device basically corresponds to that shown in FIG. 2 except for the difference that in this exemplary embodiment the electrodes 31*b*, 31*c* and 32*b*, 32*c* are each arranged on the lower side or upper side of the piezoelectric layers 31*a*, 32*a*. Additional insulation 39 is provided between electrodes 31*b* and 31*c* and 32*b* and 32*c*. Identical reference numerals are also used where identical parts are designated.

In contrast to the exemplary embodiment of FIG. 2 the sensor elements 31-32 and heating elements 311-312 are arranged on a membrane 30 in the exemplary embodiment of FIG. 3. This is a stand-alone membrane which has been produced by back processing of an Si wafer 35. This may take place by back etching by way of example, an oxide or nitride layer acting as an etching stop and forming the membrane in the finished array.

This exemplary embodiment has the particular advantage that heat losses can be prevented in the carrier substrate. The membrane 30 has a thermally insulating effect, so the heat loss in the heating device can be limited. With a given heating power the dimensions of the heating element can be reduced hereby. This contributes considerably to miniaturization.

FIG. 4 shows a third exemplary embodiment of a device according to the invention in cross-section which is also constructed as a 3.times.3 sensor array 4 for detection of a substance. The reference numerals used correspond to those in FIGS. 2 and 3 where identical parts are designated. In this exemplary embodiment the sensor elements of the second exemplary embodiment are arranged to form a 3×3 array. Electrodes 33*b* and 33*c* are each arranged on the lower side or upper side of the piezoelectric layer 33*a*. Further coating layers 301-303 correspond to coating layer 201-209 in FIG. 2*a*.

In contrast to the first and second exemplary embodiments of the device according to the invention the heating elements 211-219 and the sensor elements 31-33 are arranged on a surface micromechanism 48 in the third exemplary embodiment. This surface micromechanism 48 comprises a base which is formed by the substrate 40. Cavities 41*a*-41*c* for insulation are introduced by selective etching of the substrate from the top by removing a sacrificial layer 45*a*-45*c* by etching. Corresponding channels, for example channels 421*a*-421*c* are provided in the membranes 42*a*-42*c* for this purpose. After the etching process the channels are sealed by the cover layer 43. The result is again a respective membrane 42*a*-42*c* which provides the advantages described above in relation to thermal and acoustic insulation.

The described embodiments are geared toward the configuration of the device according to the invention as a sensor for detecting the absorption of a substance. The invention is not restricted hereto however. Other application examples relate to a component configured as a high-frequency filter, or an amplifier. Further application examples in which the initial value of a corresponding device is determined by the resonant frequency of the piezoacoustic resonator element are conceivable. The integrated configuration of piezoacoustic resonator element and heating element makes it possible to miniaturize a device of this kind. By local generation of a predefined working temperature the accuracy of the device according to the invention with respect to the value it outputs can be increased depending on the application.

Details of the structures of the above-mentioned exemplary examples can be combined with each other as a function of the envisaged application to thus provide further exemplary embodiments that are optimized for the specific application. If such modifications of the described exemplary embodiments are readily apparent to a person skilled in the art then they should be regarded as being implicitly disclosed by the above description.

An exemplary embodiment of a method for producing the device according to the invention will be described hereinafter with reference to FIG. 5.

An Si wafer element, of which the cover layer is made from silicon dioxide ($Si_xO_y/S_tO_2$), is provided with a Pt layer in step 51 by sputtering.

An electrode of the piezoacoustic resonator and a heat conductor are produced by microstructuring in step 52.

The remaining steps 53 for constructing a BAW resonator are basically known from the art and do not require detailed discussion at this point therefore. A membrane can be produced by selective etching of the back of a sacrificial layer by way of example, as has been described above with reference to FIG. 4. Further method steps comprise depositing a piezoelectric layer, applying the second electrode and appropriate contacting of the elements to produce the device.

As already mentioned it is particularly advantageous to produce the lower or upper electrode and the heating element by microstructuring the same Pt layer. It is thus possible to construct a measuring element of a temperature sensor from one layer in addition to an electrode and heating element.

In a particularly advantageous embodiment electrodes, heating element and measuring element of the sensor are formed from one layer portion which is activated in different ways according to the desired function.

An exemplary embodiment of a method for outputting a signal, which depends on a resonant frequency, will be described with reference to FIG. 6.

In step 61 a predefined working temperature of a device with piezoacoustic resonator element is adjusted, i.e. controlled, by a heating element.

In step 62 a thickness mode of vibration (i.e. bulk wave) is induced with resonant frequency by applying an alternating voltage to the electrodes of the piezoelectric layer of the piezoacoustic resonator element.

An output signal is output in step 63 as a function of the measured resonant frequency.

A method according to the invention of this kind is particularly expedient if it is configured as a method for detection of a substance. In this connection it includes the steps of combining a surface portion of the piezoacoustic resonator, which is configured for absorption of a substance, with a fluid that contains the relevant substance to be detected. Following absorption of the substance the resonant frequency is measured, and this depends on the mass of absorbed substance. This can be a differential measurement, i.e. a measurement of the resonant frequency before and after absorption of the substance. The absorption of the relevant substance in the fluid can be inferred from the measured resonant frequency. By controlling the working temperature of the device a specific substance, which is absorbed at a predefined temperature, can be selectively absorbed. This exemplary embodiment includes the method step of evaluating the measured resonant frequency to detect the relevant substance and outputting a relevant output value.

The invention claimed is:

1. A device comprising:
   at least one piezoacoustic resonator element (21-29) with at least one piezoelectric layer (21*a*-29*a*) and two electrodes (21*b*-29*b*, 21*c*-29*c*) applied to the piezoelectric layer (21*a*-29*a*), the piezoacoustic resonator element (21-29) being configured in such a manner that when a voltage is applied to the piezoelectric layer (21*a*-29*a*) by means of the electrodes (21b-29b, 21c-29c), a bulk wave of the piezoelectric layer (21a-29a) is induced with a resonant frequency;

a heating device with a heating element (211-219), integrated into the piezoacoustic resonator element (21-29), for controlling the working temperature of the device, the device is constructed in such a way that the heating element (211-219) of the heating device can also be operated as a temperature measuring element; and an evaluation device for determining the temperature from the resistance value of the temperature measuring element and which is constructed so as to be integrated into the carrier substrate, the evaluation device comprises a storage device for storing a characteristic curve that describes the temperature dependency of the resistance and a read-out device for reading out a temperature value as a function of the detected resistance value of the heating element (211-219).

2. The device as claimed in claim 1, wherein the heating element (211-219) comprises a resistance heater constructed as a layer.

3. The device as claimed in claim 2, wherein the heating element (211-219) is substantially made from platinum.

4. The device as claimed in claim 1, wherein the heating element (211-219) has a layer thickness of d<25 μm.

5. The device as claimed in claim 1, wherein the layer and the piezoacoustic resonator element (21-29) are directly constructed using layer technology on a common carrier substrate.

6. The device as claimed in claim 5, wherein the carrier substrate is made from a semiconductor material and the device is integrated on the substrate as a system-on-a-chip.

7. The device as claimed in claim 5, wherein an electrode of the resonator element (21-29) and the heating device are arranged as layers directly on the common carrier substrate.

8. The device as claimed in claim 5, wherein the carrier substrate is constructed as a membrane (30).

9. The device as claimed in claim 1, wherein the heating element (211-219) is made from a plurality of mutually joined sections which are arranged in such a way that the resonator element (21-29) and/or its surroundings can be heated from a plurality of sides of the resonator element (21-29).

10. The device as claimed in claim 9, wherein the sections are arranged at substantially the same spacing from the edge portions of the resonator element (21-29).

11. The device as claimed in claim 1, wherein the heating element (211-219) is constructed as a metal strip conductor.

12. The device as claimed in claim 5, further comprising: an acoustic reflector (210) consisting of a plurality of layers is arranged between the carrier substrate and the piezoacoustic resonator element (21-29).

13. The device as claimed in claim 1, wherein a lateral spacing between the heating element (211-219) and the piezoelectric layer (21a-29a) is less than 100 μm.

14. The device as claimed in claim 1, wherein the device is constructed as an array with a large number of piezoacoustic resonator elements (21-29) and at least one heating device.

15. The device as claimed in claim 1, wherein the heating element (211-219) and the temperature measuring element are formed by a layer which is substantially made from platinum.

16. The device as claimed in claim 1, wherein the device is constructed as a sensor element for detection of a substance, the piezoacoustic resonator element (21-29) comprising a surface portion for absorbing a substance to be detected and the resonant frequency of the resonator element (21-29) being dependent on the absorption of the substance.

17. The device as claimed in claim 16, wherein the heating device is arranged in such a position on the sensor element that the medium for measuring can be heated by the heating element (211-219).

18. The device as claimed in claim 16, wherein the heating device is arranged in such a position on the sensor element that the surface portion can be heated by the heating element (211-219).

19. The device as claimed in claim 1, wherein the layer and the piezoacoustic resonator element (21-29) are directly constructed with two intermediate layers on a common carrier substrate.

20. A method for producing a device as claimed in claim 1, with the steps of applying a metal layer to a carrier substrate and microstructuring the metal layer to create an electrode of the piezoacoustic resonator element (21-29) and a heating element (211-219) from this layer.

21. A method for outputting a signal that depends on a resonant frequency, comprising the steps of:

controlling by way of a heating element (211-219) the working temperature of a device with piezoacoustic resonator element (21-29) as claimed in claim 1, inducing a bulk wave of a piezoelectric layer (21a-29a) of the piezoacoustic resonator element (21-29) with resonant frequency, outputting an output signal as a function of the measured resonant frequency.

22. The method as claimed in claim 21, wherein the method is configured as a method for detection of a substance, with the step of combining a surface portion of the piezoacoustic resonator configured for absorption of the substance with a fluid that contains the substance to be detected, measuring the resonant frequency as a function of the quantity of absorbed substance, and evaluating the measured resonant frequency for detection of the substance.

23. The method as claimed in claim 21, further comprising: a step of measuring the working temperature of the piezoacoustic resonator element (21-29).

24. The method as claimed in claim 23, further comprising: a step of regulating the working temperature of the piezoacoustic resonator element (21-29).

* * * * *